United States Patent [19]

Senyei et al.

[11] Patent Number: 5,185,270
[45] Date of Patent: Feb. 9, 1993

[54] FETAL FIBRONECTIN PREGNANCY TEST

[75] Inventors: Andrew E. Senyei, Santa Ana; Nelson N. H. Teng, Hillsborough, both of Calif.

[73] Assignee: Adeza Biomedical Corporation, Sunnyvale, Calif.

[21] Appl. No.: 282,426

[22] Filed: Dec. 12, 1988

Related U.S. Application Data

[63] Continuation-in-part of Ser. No. 121,900, Nov. 17, 1987, abandoned.

[51] Int. Cl.$^5$ .................. G01N 33/53; G01N 33/48
[52] U.S. Cl. ............................. 436/510; 435/709; 436/518; 436/65; 436/814; 436/86
[58] Field of Search ............ 43/7; 436/510, 518, 436/547, 548, 63, 65, 814, 86

[56] References Cited

U.S. PATENT DOCUMENTS

| | | | |
|---|---|---|---|
| 4,279,992 | 7/1981 | Boguslaski et al. | 435/7 |
| 4,325,867 | 4/1982 | Eberle et al. | 260/112 B |
| 4,675,286 | 6/1987 | Calenoff | 435/7 |

FOREIGN PATENT DOCUMENTS 60-091264  5/1985  Japan .
1107051  8/1984  U.S.S.R. .

OTHER PUBLICATIONS

H. Gray, *Gray's Anatomy*, Bounty: New York, pp. 1025-1031 (1977).
*Int. J. Cancer:* 27, 763-767 (1981) "Fibronectin From Human Germ-Cell Tumors Resembles Amniotic Fluid Fibronectin" by Ruoslahti, et al.
Wisdom, G. B., *Clinical Chemistry*, vol. 22(8), pp. 1243-1255 (1976).
Oellerich, M., J. Clin. Chem. Clin. Biochem., vol. 22(12), pp. 895-904 (1984).
Atherton, B. et al, *Cell* 25:133-141 (1981).
Barnea, E. et al, "β-HCG and Other Chemical Parameters of Ectopic Pregnancy". Maryland: Aspen Publishers, Inc. (1986).
Batzer, F., *Contemporary Ob/Gyn* 7-16 (1987).
Bell, S., *Human Reproduction* 1:129-143 (1986).
The Human Placenta, Boyd, J. et al. New York: MacMillan Press (1970).
Bray, B. *Biochem. J.* 226:811-815 (1985).
Bulmer, J. et al, *Placenta* 6:127-140 (1985).
Bützow, R. et al, *Human Reproduction* 1:287-289 (1986).
Chiquet-Ehrismann, R. et al, *Cell* 47:131-139 (1986).
Cossu, G. et al, *J. Biol. Chem.* 258:5603-5607 (1983).
Cruz, R. et al, *J. Clin. Endocrinol. Metab.* 64:433-440 (1987).
Davis, F. et al, *Proc. Natl. Acad. Sci. USA* 80:2926-2930 (1983).
Fletcher, J. *Primary Care* 13:667-677 (1986).
Fritz, M. et al, *Fertility and Sterility* 47:584-589 (1987).
Ganrot, P., *Scand. J. Clin. Lab. Invest.* 29:83-88 (1972).
Gelletlie, R. et al, *Clin. Chem.* 32:2166-2170 (1986).
Hayashi, M. et al, *J. Biol. Chem.* 256:11292-11300 (1981).
Hess, L. et al, *Obstet. Gynecol.* 68:25-28 (1986).

Immunoassays for the 80s, Voller et al (ed.). Baltimore: University Park Press (1981).
Johnson, P. et al, *The Journal of Immunology* 132:1608-1610 (1984).
Kiyotoshi, S. et al, *Biochem. Biophys. Res. Comm.* 116:534-540 (1983).
Kuusela, P. et al, *Scand. J. Immunol.* 12:331-337 (1980).
Liu, M. et al, *Proc. Natl. Acad. Sci. USA* 82:34-37 (1985).
Matsuura, H. et al, *Proc. Natl. Acad. Sci. USA* 82:6517-6521 (1985).
McCoshen, J. *Contemporary Ob/Gyn* May, 1987:94-117.
McSweeney, D. et al, *Fertility and Sterility* 18:866-869 (1967).
Nakabayashi, H. et al, *Cancer Res.* 42:3858-3863 (1982).
Pregnancy Proteins: Biology, Chemistry and Clinical Application, Grudzinskas, J. et al (ed.). New York: Academic Press (1982).
Ruoslahti, E. et al, *Int. J. Cancer* 27:763-767 (1981).
Sandler, S. et al, *S. A. Medical Journal* (Sep. 1977): 487-492.
Sekiguchi, K. et al, *J. Biol. Chem.* 258:3967-3973 (1983).
Sekiguchi, K. et al, *J. Biol. Chem.* 260:5105-5114 (1985).
Sinosich, M. et al, *Obstet. and Gynecol. Survey* 40:273-282 (1985).
Stern, P. et al, *J. Immunol.* 137:1604-1609 (1986).
Ulloa-Aguirre, A. et al, *J. Clin. Endocrin. Metab.* 64:1002-1009 (1987).
Van Kooij, R. et al, *Fertility and Sterility* 34:226-233 (1980).
Vuento, M. et al, *Hoppe-Seyler's Z. Physiol. Chem.* 361:1453-1456 (1980).
Wagner, D. et al, *J. Biol. Chem.* 256:11708-11715 (1981).
Yeh, H. et al, *Radiology* 161:463-467 (1986).
Yuen, H., "Clinical Applications of the HCG-β Subunit Assay in Obstetrics and Gynecology", Current Problems in Obstetrics, Gynecology and Fertility. Chicago: Year Book Medical Publishers, Inc. (Sep. 1985).
Zardi, L. et al, *Int. J. Cancer* 25:325-329 (1980).
Zhu, B. et al, *J. Biol. Chem.* 259:3962-3970 (1984).

*Primary Examiner*—Sam Rosen
*Attorney, Agent, or Firm*—Laura Terlizzi

[57] ABSTRACT

A method for determining normal intrauterine pregnancy during the first 20 weeks of pregnancy comprises obtaining a test sample; and determining the presence of a fetal restricted antigen in the sample. The test sample is removed the vaginal cavity in the vicinity of the cervical canal and/or the cervical os. One fetal restricted antigen is fetal fibronectin.

In one embodiment of this invention, the test sample is contacted with an insoluble support to which anti-(fetal restricted antigen) antibody is adhered, and the fetal restricted antigen binding to the support is determined. Alternatively, the test sample is contacted with an insoluble support to which is adhered an antibody which binds a class of substances including the fetal restricted antigen; and the fetal restricted antigen binding to the support is determined. Reagents and reagent kits are also included.

10 Claims, No Drawings

18
FETAL FIBRONECTIN PREGNANCY TEST

RELATIONSHIP TO COPENDING APPLICATION

This application is a continuation-in-part of copending application Ser. No. 121,900, filed Nov. 17, 1987, now abandoned.

FIELD OF THE INVENTION

This invention relates to methods, reagents and kits for early determination of pregnancy. In particular, this invention is directed to the determination of normal pregnancy in the uterus during weeks 1 to 20 of pregnancy by testing a sample for the presence of a fetal restricted antigen.

BACKGROUND OF THE INVENTION

A wide variety of tests have been developed for the determination of pregnancy. Commercial early pregnancy determinations include the rabbit ovulation test of urine (5.5 wk), rat ovarian hyperemia test of urine (5.5 wk), hemagglutination inhibition latex particle test of urine (5.5 wk), RIA (radioimmunoassay) test of blood using competition with $^{125}$I labeled hCG for anti-(hCG) antibodies (3.5 wk), RIA test of blood using competition with $^{125}$I labeled hCG for anti-($\beta$-hCG) antibodies (3.5 wk), and RRA (radioreceptor assay) test of blood using competition with $^{125}$I labeled hCG for specific receptor sites. The RIA tests have been refined to provide qualitative results the same day but require an additional day to determine the exact titer of hCG or $\beta$-hCG in the serum. The RRA assay is more rapid, but is currently less sensitive than the RIA test.

Home pregnancy tests for hCG in urine include a variety of enzyme immunoassays, hemagglutination inhibition, and antibody-antigen agglutination tests which are effective to indicate pregnancy from 0 to 9 days after a missed period. Confirmation by physician is recommended, particularly to determine abnormal gestation such as ectopic pregnancy.

HCG is produced by the fetal trophoblast and passes from the fetal blood into the mother's blood through the intervillous space in the placenta. HCG levels in maternal blood and urine are often detectable at about 3 weeks. The sensitivity of the serum or urine hCG tests is limited because the amount of hCG produced is determined by the amount of trophoblastic tissue, and by the dilution of the hCG in the maternal fluids. Until development of the $\beta$-hCG specifically binding antibody, cross-reaction with LH also placed a limit on the level of sensitivity.

We have discovered that normal uterine pregnancies can be determined early in the gestation cycle and with a high reliability by testing a sample for the presence of fetal restricted antigens, that is, antigenic and non-antigenic compounds or materials which are produced in the placental tissue and which do not pass in any substantial amounts into the maternal blood. Included in this class of antigens are fetal fibronectins.

DESCRIPTION OF THE PRIOR ART

Cervical mucus has been tested to determine a variety of conditions. Cervical mucus chloride levels have been monitored to determine pregnancy by McSweeney, D. et al, *Fertility & Sterility*. 8:866–869 (1967). Similar methods are described in U.S. Pat. Nos. 3,436,186 and 3,434,801 and Great Britain Patent Applications No. 1,103,401 and 1,103,403. Cervical mucus has also been tested for glucose levels (U.S. Pat. No. 3,116,223 and Great Britain Application 1,240,884), water level (U.S. Pat. No. 4,151,833), guaiacol peroxidase (U.S. Pat. No. 4,614,715), for variations in chemical composition using NMR (U.S. Pat. No. 4,390,633) and infrared (Japanese Application 62,005,340), and for malignant tumors (treating mucus extract with haemostatic mixture in USSR Patent application 597,107). A wide variety of methods have been devised to measure the physical properties of cervical mucus such as mucus fibrosity in French Application 2,346,718; rheological properties in U.S. Pat. No. 3,979,945; resistance to separation of two opposed plates in U.S. Pat. No. 3,926,037; index of refraction in USSR application 1,146,036; and electrical resistivity in Romanian application 71,545. Ionic conductance of cervical secretions of cows was measured to determine pregnancy in U.S. Pat. No. 4,039,934.

Van Kooij, R. et al, *Fertil.Steril.* 34:226–233 (1980) reports a study of the hexose and protein concentrations of human cervical mucus during the menstrual cycle, finding the concentration of mucous glycoprotein rises after the ovulatory phase, but less than the concentration of the other proteins. McCoshen, J. et al, *Contemporary OB/GYN*. pp 94–117 (May, 1987) describes the production levels and the physical changes in cervical mucus during menstrual cycle correlated with serum levels of FSH, LH, estradiol and progesterone levels. The principal components of cervical mucus are reported as amino acids; enzymes such as alkaline phosphatase and lactate dehydrogenase; hormones such as estradiol, progesterone, and prolactin; inorganic salts such as sodium chloride; lipids; mucin; organic salts and acids such as sialic acid; soluble proteins such as albumin, IgA and IgG; sugars such as glucose; trace elements such as Cu and Zn; and water. Sandler, S., et al, *S.Afr.Med.J.* 52:487 (1977) reports the correlation of plasma estradiol, estriol, progesterone, hCG, human placental lactogen (hPL), and karyopyknotic index (KPI) and cervical mucus patterns serially throughout pregnancy. In normal pregnancy there is usually no ferning.

U.S. Pat. No. 4,686,180 describes the preparation of oncofetal specific monoclonal antibodies. These antibodies do not bind preferentially with fetal restricted antigens and are thus not anti-(fetal restricted antigen) antibodies.

Matsuura, H. and Hakomori, S., *Proc.Natl.Acad.Sci.USA*. 82:6517–6521 (1985) describe the discovery of a fetal fibronectin which binds preferentially with a monoclonal antibody FDC-6, and that this antibody does not bind significantly with normal adult fibronectins. The fetal fibronectin was found in placenta, amniotic fluid and fetal connective tissue, as well as a number of tumors. The antibody did not bind with constituents of normal adult plasma and adult tissue. Structural differences between the fetal fibronectin and adult fibronectins were described. Other references relating to this discovery are Ali, I. et al, *J.Biol.Chem.* 256:7671–7677 (1981); Wagner, D. et al, *J.Biol.Chem.* 256:11798–11715 (1981); Dekiguchi, K. and Hakomori, S., *J.Biol.Chem.* 258:3967–3973 (1983); Hayashi, M. et al, *J.Biol.Chem.* 256:11292–11300 (1981); Atherton, B. et al, *Cell*. 25:133–141 (1981); Ruoslahti, E. et al, *Int.J.Cancer*. 27:763–767 (1981); Zhu, B. et al, *J.Biol.Chem.* 259:3962–3970 (1984); Cossu, G. et al, *J.Biol.Chem.* 258 5603–5607 (1983); Murayama, K., Hakomori, S. et al,

*Glycoconjugate.* 1:155-169 (1984); Teng, M. et al, *J.Cell-.Biol.* 784-791 (1979); Liu, M. et al, *Proc.Natl.Acad.Sci.* 82:34-37 (1985); Kiyotoshi, S., Hakomori, S. et al, *Biochem.Biophys.Res.Comm.* 116:534-540 (1983). Sekiguchi, K., Hakomori, S., et al, *J.Biol.Chem.* 260:5105-5114 (1985); Zardi, L., et al, *Int.J.Cancer.* 25:325-329 (1980); and Nakabayashi, H. et al, *Canc. Res.* 42:3858-3863 (1982); Dot, I. *Gann.* 67:1-10 (1976). Kuusela, P., et al, *Scand.J.Immunol.* 12:331-337 (1980) also discloses a monoclonal antibody binding preferentially with amniotic fluid fibronectin (fetal fibronectin) and a method for preparing the hybridoma therefor.

Immunoassay reagents and procedures have been developed for determining the presence and amount of a wide variety of antigenic and non-antigenic materials in diverse body fluids and tissues. These fall into a broad classification of homogeneous and heterogeneous methods, and are summarized in U.S. Pat. No. 4,279,992 and in IMMUNOASSAYS FOR THE 80s. Voller, A. et al (editors), Baltimore: University Park Press (1981). ELISA immunoassays are described by Maggio, et al, ENZYME-IMMUNOASSAY. Boca Raton: CRC Press pp 172-176 (1980).

A wide variety of nonrestricted pregnancy antigens and antibodies which bind preferentially therewith are set forth in PREGNANCY PROTEINS: BIOLOGY, CHEMISTRY AND CLINICAL APPLICATION. Grudzinskas, J. et al (editors), New York: Academic Press (1982) and the publications cited therein. Examples of identified fetal antigens are human chorionic gonadotropin (hCG), human chorionic thyrotropin (hCT), human placental lactogen (hPL), Schwangerschafts-spezifizisches glykoprotein I or pregnancy specific $\epsilon_1$-glycoprotein (SPI), pregnancy-associated plasma protein A (PAPP-A), pregnancy-associated plasma protein B (PAPP-B), heat-stable alkaline phosphatase (HSAP) (S, I, and F phenotypes), cystine aminopeptidase (CAP), placental protein 5 (PP5), placenta specific $\alpha_1$-microglobulin (PAMGI), placenta specific $\alpha_2$-microglobulin (PAMG2), pregnancy associated $\beta_1$-macroglobulin ($\beta_1$-PAM), pregnancy associated $\alpha_2$-macroglobulin ($\alpha_2$-PAM), human chorionic luteinizing hormone-releasing factor (hCLRF), human chorionic thyrotropin-releasing hormone (hCTRH), human chorionic growth hormone-releasing inhibiting hormone (somatostatin), all of these being fetal proteins which have been purified and characterized, and which are produced by the placenta. These unrestricted pregnancy antigens are compounds and substances found in significant amounts in the maternal plasma and serum and are not fetal restricted antigens.

Isolation and diagnostic examination of fetal cells from cervical samples obtained by lavage of the uterine cavity is described in U.S. Pat. No. 4,675,286.

An immunological method for determining total fibronectin in samples is described in Japanese Patent Application 60091264 (DIALOG database file 351, WPI Acc. No. 85-161617/27). A non-immunological method is described in USSR Patent Application No. 1107051 (DIALOG database file 351, WPI Acc. No. 85-055390/09). Separation of total fibronectin (also identified as $\alpha_2$-sb-glycoprotein, cold-soluble protein and LETS-protein) by affinity chromatography is described in U.S. Pat. No. 4,325,867. ATCC HB 91 (American Type Culture Collection, Rockville, Md.) is a hybridoma clone which produces an anti-(cellular and plasma fibronectin) antibody.

All of the patents and publications listed above in the Background of the Invention, the Description of the Prior Art, and the references cited therein are hereby each incorporated by reference in their entireties.

SUMMARY OF THE INVENTION

The method for determining normal pregnancy during the first 20 weeks of pregnancy comprises obtaining a sample from the vaginal cavity; and determining the presence of a fetal restricted antigen in the sample. The sample is removed in the vicinity of the cervical canal and/or the cervical os. One fetal restricted antigen is fetal fibronectin.

In general, the method comprises interacting the fetal restricted antigen in a test sample with an anti-(fetal restricted antigen) antibody for a time sufficient to permit antigen-antibody binding to occur; and determining the presence or absence of said binding.

In one embodiment of this invention, the test sample is contacted with an insoluble support to which anti-(fetal restricted antigen) antibody is adhered for a time sufficient to permit antigen-antibody binding to occur, and the sample is removed from the support. The insoluble support is then contacted with an antibody which binds with the fetal restricted antigen or the fetal restricted antigen class (i.e., a secondary antibody) for a time sufficient to permit antigen-antibody binding to occur, and the unbound secondary antibody is removed from the support. The presence or absence of secondary antibody on the insoluble support is then determined. The secondary antibody can have a physically detectable label which can be measured directly on the insoluble support. Alternatively, the secondary antibody can be unlabeled, and the secondary antibody can be determined by contacting the insoluble support with a labeled antibody or antibody fragment which binds preferentially with the secondary antibody (i.e., a tertiary antibody), removing unbound labeled tertiary antibody from the support, and determining the presence of the label on the insoluble support.

In an alternate embodiment of this invention, the test sample is contacted with an insoluble support to which is adhered an anti-(fetal restricted antigen class) antibody for a time sufficient to permit antigen-antibody binding to occur, and removing the sample from the support. The insoluble support is then contacted with an anti-(fetal restricted antigen) antibody for a time sufficient to permit antigen-antibody binding to occur, and removing unbound anti-(fetal restricted antigen) antibody from the support. Finally, the presence of anti-(fetal restricted antigen) antibody on the insoluble support is determined. The anti-(fetal restricted antigen) antibody can have a physically detectable label, in which event, the label adhering to the insoluble support can be determined. Alternatively, the anti-(fetal restricted antigen) antibody can be unlabeled, and the insoluble support can be contacted with a labeled tertiary antibody or antibody fragment which binds preferentially with the anti-(fetal restricted antigen) antibody, the unbound labeled antibody is removed from the support, and the presence of the label on the insoluble support is determined.

Competition embodiments of this invention using labeled reagent fetal restricted antigen comprise contacting a mixture of the test sample and labeled reagent fetal restricted antigen with an anti-(fetal restricted antigen) antibody adhered to an insoluble support, and determining the amount of label which either binds with the insoluble support or remains in the solution phase.

Competition embodiments of this invention using labeled anti-(fetal restricted antigen) antibodies can be of more than one type. One embodiment using anti-(fetal restricted antigen) antibody bound to the insoluble support comprises contacting a mixture of the test sample and labeled anti-(fetal restricted antigen) antibody with anti-(fetal restricted antigen) antibody adhered to an insoluble support, and determining the amount of label which either binds with the insoluble support or remains in the solution phase. Another embodiment uses reagent fetal restricted antigen bound to the insoluble support, and comprises contacting a mixture of the test sample and labeled anti-(fetal restricted antigen) antibody with a fetal restricted antigen adhered to an insoluble support, and determining the amount of label which either binds with the insoluble support or remains in the solution phase.

Pregnancy testing reagents include insoluble supports to which are adhered anti-(fetal restricted antigen class) antibodies such as anti-(fibronectin) antibodies, anti-(fetal restricted antigen) antibodies such as anti-(fetal fibronectin) antibodies, and the like. This invention also includes kits comprising one of the above reagents, alone or in combination with labeled antibodies. One preferred embodiment of a kit of this invention comprises an anti-(fibronectin) antibody adhered to an insoluble support in combination with a labeled anti-(fetal fibronectin) antibody. Another preferred embodiment of a kit of this invention comprises an anti-(fibronectin) antibody adhered to an insoluble support, in combination with a labeled anti-(fetal fibronectin) antibody.

DETAILED DESCRIPTION OF THE INVENTION

The method of this invention involves the detection of a uniquely fetal or placental focused material in a test sample. We have discovered that detectable amounts of these materials are present in normal uterine pregnancy in detectable levels early in gestation. Since the fetal restricted antigens are not present in significant quantities in the maternal blood, the presence of maternal blood in the sample does not interfere with the test.

The term "fetal restricted antigen" as used hereinafter is defined to mean this uniquely fetal or placental derived material, which is either not present in maternal serum, plasma or urine, or is not present in significant amounts in maternal serum, plasma or urine. Any substance meeting this definition is intended to be included within the meaning of the term, including both antigenic materials and proteins and other substances which are not antigenic in their purified form but which have unique epitopes which can be bound with antibodies preferentially binding thereto. An example of a fetal restricted antigen is the fetal fibronectin which binds preferentially with the FDC-6 monoclonal antibody described by Matsuura, H. and Hakomori, S., *Proc.Natl. Acad.Sci.USA.* 82:6517-6521 (1985).

The term "fetal restricted antigen class" as used herein is defined to mean the class or group of antigens of which the "fetal restricted antigen" is a member. For example, fetal fibronectin is a fetal restricted antigen member of the human fibronectin group or class.

The term "nonrestricted pregnancy antigen" as used herein is defined to mean compounds or substances which can be detected in body fluids such as serum, plasma, and urine to indicate pregnancy and which are present in significant amounts in maternal serum, plasma or urine.

The term "antibody" as used herein is defined to include antibodies of classes IgG, IgM, IgA, IgD, and IgE, and preferentially binding fragments and hybrid derivatives of antibodies including Fab, and F(ab')$_2$ fragments of antibodies. Antibodies may be polyclonal or monoclonal. Generally, monoclonal antibodies are preferred for use in the methods of this invention.

A test sample which is to be assayed is removed from the vaginal cavity in the vicinity of the cervical canal or the cervical os, and the sample is assayed to determine the presence or quantity of fetal restricted antigen in the sample. The test sample generally comprises fluid and particulate solids, and may contain vaginal or cervical mucus, other vaginal or cervical secretions, cells or cell debris, amniotic fluid, or other fetal or maternal materials. The test sample is removed with a swab having a dacron or other fibrous tip, aspirator, suction device, lavage device or the like and is transferred to a suitable container for storage and transport to the testing laboratory.

It is important that the test sample be dispersed in a liquid which preserves the sensitive protein analytes which are unstable in the sampled composition. The storage and transfer medium should prevent decline in the protein analyte level during storage and transport. A suitable preserving solution for storage and transfer consists of 0.05M Tris-HCl, pH 7.4; 0.15M NaCl, 0.02% NaN$_3$, 1% BSA, 500 Kallikrein Units/mL of aprotinin, 1 mM phenylmethylsulfonyl fluoride (PMSF) and 5 mM EDTA, and is described in U.S. patent application Ser. No. 244,969, filed Sep. 15, 1988, the entire contents of which are hereby incorporated by reference.

Detection of the fetal restricted antigen can be achieved by binding the fetal restricted antigen in a test sample with an antibody which binds preferentially with an epitope of the fetal restricted antigen, and determining the presence or absence of this binding. Immunological methods are most convenient for carrying out this method because of their specificity. The term "immunoassays" as used herein is defined to mean any method using a preferential binding of a fetal restricted antigen with a second material, a binding partner, usually an antibody or another substance having an antigen binding site which binds preferentially with an epitope of the fetal restricted antigen. Preferential binding as used herein refers to binding between binding partners which is selective and generally specific, and which demonstrates less than 10%, preferably less than 5%, cross-reactive nonspecific binding. For example, when the analyte is fetal fibronectin, the anti-(fetal fibronectin) antibody is generally less than 10%, and preferably less than 5%, cross-reactive with adult fibronectin. Included within the scope of this invention are all immunoassay methods including this step, including but not limited to sandwich, competition, agglomeration, precipitation, transistor bridge probe, light disturbing, light scattering, and ultrasonic probe immunoassays, for example.

In one embodiment of this invention, the test sample is contacted with an insoluble support to which anti-(fetal restricted antigen) antibody is adhered to effect binding of fetal restricted antigen in the sample to the insoluble support. The insoluble support is then contacted with an unlabeled or labeled anti-(fetal restricted antigen) antibody, which binds with the fetal restricted antigen adhering to the insoluble support to detect and measure the captured fetal restricted antigen.

An antibody which binds with a class of substances including the analyte fetal restricted antigen can be substituted for the anti-(fetal restricted antigen) antibody capture antibody or the anti-(fetal restricted antigen) sandwiching antibody. For example, anti-(fetal fibronectin) antibody can be adhered to the insoluble support, and labeled or unlabeled anti-(fibronectin) antibody can be used to detect the captured antigen. Alternatively, the test sample is contacted with an insoluble support to which is adhered an antibody which captures a group of substances which includes the fetal restricted antibody to be measured. The insoluble support is then contacted with an unlabeled or labeled anti-(fetal restricted antigen) antibody to detect and measure the captured fetal restricted antigen. For example, anti-(fibronectin) antibody can be adhered to the insoluble support, and labeled or unlabeled anti-(fetal fibronectin) antibody is used to detect the captured antigen.

Alternatively, the sample is tested by a competition immunoassay procedure. The test sample can be mixed with labeled reagent antibody or antigen and incubated with an insoluble support to which an anti-(fetal restricted antigen) antibody or reagent fetal restricted antigen is adhered, competition occurring between the reagents for binding with the test sample analyte. The label ultimately adhering to the insoluble support or remaining in the solution is then determined.

This invention will be described hereinafter with respect to the detection of fetal fibronectin, for purposes of clarity, and not by way of limitation: the detection of any fetal restricted antigen is intended to be within the scope of this invention.

The anti-(fetal restricted antigen) antibody can be obtained from fetal restricted antigens, preferably from highly purified fetal restricted antigens, by conventional antiserum or monoclonal techniques. Fetal fibronectin is purified from amniotic fluid as described by Engvall and Ruoslahti, *Int.J.Cancer.* 20:1-5 (1977). Anti-(fetal fibronectin) antibody can be derived from fetal fibronectin by conventional antiserum techniques or by monoclonal antibody techniques.

Polyclonal anti-(fetal restricted antigen) antibody can be obtained by immunizing an animal such as a rabbit, guinea pig, rat or goat with concentrated fetal restricted antigen, such as fetal fibronectin, removing serum from the immunized animal, and separating the immunoglobulins from the serum, for example by ammonium sulfate precipitation. The principal antibodies useful in the method of this invention are IgG and IgM antibodies, although the IgD, IgE and IgA antibodies can also be used if available in sufficient quantity. The fetal fibronectin antibodies are then affinity purified using conventional affinity chromatography techniques such as those described by Mishell and Shilgi in SELECTED METHODS IN CELLULAR IMMUNOLOGY. San Francisco: Freeman (1980), Goding, J., MONOCLONAL ANTIBODIES: PRINCIPLES AND PRACTICE. New York: Academic Press pp 111-114 (1983), and Parikh, I., et al, C&EN (Aug. 26, 1985), the entire contents of each of which are hereby incorporated by reference. Suitable adsorbents for use in affinity chromatography include cross-linked agarose and cross-linked polyacrylamides to which the fetal restricted antigen antibody is covalently bonded. For removal of antibodies cross-reacting with adult fibronectins, the antibody serum is passed through columns to which are coupled adult fibronectins. A portion of the eluant containing the remaining antibody can then be passed through a fetal fibronectin column and eluted to yield the affinity purified antibody.

In these procedures, the antibody solution can be applied to the column in a phosphate buffered saline solution, and the antibodies can be eluted with a 2.5M NaSCN solution, pH 8.0. Antibody concentration, if desired, can be achieved by negative pressure dialysis or ultrafiltration. The antibody solution is stable at temperature of 4° C. or less. Repetition of the column separation procedures is continued until the desired separation and purity is achieved.

Monoclonal anti-(fetal restricted antigen) antibody can be obtained by the methods of Galfre and Milstein, *Meth.Enzym.* 73:1 (1981), immunizing mice with fetal restricted antigens to obtain the spleen cells for hybridization. Suitable procedures are described by Goding, MONOCLONAL ANTIBODIES: PRINCIPLES AND PRACTICE. New York: Academic Press (1983) pp 56-97, the entire contents of which are hereby incorporated by reference. For production of fetal fibronectin, the procedures described by Matsuura and Hakomori, *Proc.Natl.Acad.Sci.USA* 82:6517-6521 (1985) can be followed, replacing the tumor fibronectin with fetal fibronectin.

Anti-(fetal restricted antigen class) antibodies of both polyclonal and monoclonal varieties are generally well known and available either commercially or from publicly available hybridoma deposits. For example, anti-(fibronectin) monoclonal antibodies can be derived from clone samples from ATCC HB 91 (American Type Culture Collection, Rockville, Md.). Such antibodies are also described in Japanese Patent Application 60091264 (DIALOG database file 351, WPI Acc. No. 85-161617/27) and U.S. Pat. No. 4,325,867.

Preferentially binding antibody fragments suitable for use in the kit and method of this invention can be made from the respective monoclonal or polyclonal antibodies by conventional enzyme or chemical fragmentation procedures. Suitable procedures are described by Tijssen, P. LABORATORY TECHNIQUES IN BIOCHEMISTRY AND MOLECULAR BIOLOGY: PRACTICE AND THEORIES OF ENZYME IMMUNOASSAYS. New York: Elsevier (1985), for example.

Antigen and antibody reagents can be bonded to an insoluble support by conventional processes. Antigen binding methods suitable for binding antigens to insoluble supports such as those described in U.S. Pat. Nos. 3,234,096, 3,236,732, 3,309,275, 3,873,683, 3,991,175, 4,003,988, 4,016,250, 4,033,723, 4,071,314, 4,348,207, and 4,419,453, for binding antigens to latex particles and erythrocytes, for example. Procedures for binding of antibodies to insoluble supports are described in U.S. Pat. Nos. 3,551,555, 3,553,310, 4,048,298 and RE-29,474, and by Tijssen, PRACTICE AND THEORY OF ENZYME IMMUNOASSAYS. Elsevier Science Publishers, (1985) pp 297-328, for example. Procedures for binding of antibodies to polystyrene by adsorption are described in U.S. Pat. Nos. 3,646,346 and 4,092,408, for example. For purposes of clarity and not by way of limitation, the binding procedures are described hereinafter with respect to binding antibodies to insoluble supports. These procedures are equally suitable for binding the fetal restricted antigens to insoluble supports.

A variety of materials can be used as the insoluble support, the primary consideration being the binding of the reagent fetal restricted antigen, anti-(fetal restricted antigen) antibody or anti-(fetal restricted antigen class) antibody to the surface, the absence of interference with the reagent binding reaction or with other reactions which can be employed to determine the presence and extent of the binding reaction. Organic and inorganic polymers, both natural and synthetic, can be used as the insoluble support. Examples of suitable polymers include polyethylene, polypropylene, polybutylene, poly(4-methylbutylene), butyl rubber, silastic polymers, polyesters, polyamides, cellulose and cellulose derivatives (such as cellulose acetate, nitrocellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, rayon, nylon, polyvinylbutyrate, polyformaldehyde, etc. Other materials which can be used as the insoluble support can the latexes of the above polymers, silica gel, silicon wafers, glass, paper, insoluble protein, metals, metalloids, metal oxides, magnetic materials, semi-conductive materials, cermets and the like. In addition are included substances which form gels, such as proteins such as gelatins, lipopolysaccharides, silicates, agarose, polyacrylamides or polymers which form several aqueous phases such as dextrans, polyalkylene glycols (alkylene with 2 to 3 carbon atoms) or surfactants, e.g. amphophilic compounds such as phospholipids, long chain (12–24 carbon atoms) alkyl ammonium salts and the like.

A preferred diagnostic support of this invention comprises a nylon or nitrocellulose membrane. An alternate diagnostic support is made from polystyrene, styrene copolymers such as styrene-acrylonitrile copolymers, or polyolefins such as polyethylene or polypropylene, and acrylate and methacrylate polymers and copolymers.

The anti-(fetal restricted antigen) reagent antibody, anti-(fetal restricted antigen class) antibody, or reagent fetal restricted antigen can be bound to the insoluble support by adsorption, ionic bonding, van der Waals adsorption, electrostatic bonding, or other non-covalent bonding, or it can be bound to the insoluble support by covalent bonding. A particularly advantageous support for this procedure comprises a microtiter plate having a plurality of wells. The well surface or plastic cup inserts therein can constitute the antigen or antibody support. If the determination will require the use of fluorometric measurements, the microtiter plate or the well inserts are advantageously opaque to light so that excitation light applied to a well does not reach or influence contents of the surrounding wells.

Procedures for non-covalent bonding of reagents are described in U.S. Pat. No. 4,528,267. Procedures for covalently bonding antibodies and antigens to insoluble supports are described by I. Chibata in IMMOBILIZED ENZYMES. Halsted Press: New York (1978) and A. Cuatrecasas, *J.Bio.Chem.* 245:3059 (1970), the entire contents of which are hereby incorporated by reference. The surface can be coated with a protein and coupled with the antibody or antigen using procedures described in U.S. Pat. No. 4,210,418 using glutaraldehyde as a coupling agent, for example. In a still further procedure, the well can be coated with a layer having free isocyanate groups such as a polyether isocyanate, and application of the antibody or antigen in aqueous solution thereto effects the requisite bonding. In a still further procedure, the antibody or antigen can be coupled to a hydroxylated material by means of cyanogen bromide as described in U.S. Pat. No. 3,720,760.

The insoluble supports are preferably "blocked" to reduce nonspecific binding. The choice of suitable blocking agents is determined by the type of insoluble support. For example, for polystyrene supports, suitable blocking agents include water-soluble non-immune animal proteins and polyamino acids. Suitable water-soluble non-immune animal proteins include albumins such as bovine serum albumin (BSA), human, rabbit, goat, sheep, and horse serum albumins; and other animal proteins such as fetal calf serum, ovalbumin, fibrinogen, thrombin, transferrin, glycoproteins, and the like. Suitable water-soluble polyamino acids include polymers of one or more amino acids such as lysine, glutamic acid, alanine, histidine, methionine, proline, and the like.

The same blocking agents can also be used for nylon and nitrocellulose supports. However, a preferred blocking agent for nitrocellulose or nylon membrane supports is non-fat milk or casein. An optimum blocking agent for these membrane supports is an aqueous solution containing 1 to 5 wt. % non-fat dried milk and nonionic surfactants such as polyoxyethylene sorbitan derivatives and polyoxyethylene ethers.

The labeled reagent fetal restricted antigen, anti-(fetal restricted antigen) antibody, anti-(fetal restricted antigen class) antibody or anti-(sandwiching antibody) antibody reagents of this invention can be prepared by conventional procedures for attaching labels to proteins, preferably with suitable protection of antibody binding sites. The labels can be bonded or coupled to the protein reagents by chemical or physical bonding. Ligands and groups which can be conjugated to the antibodies of this invention include elements, compounds or biological materials which have physical or chemical characteristics which can be used to distinguish the reagents to which they are bonded from compounds and materials in the sample being tested.

Labeling procedures are described hereinafter with respect to labeling antibodies for purposes of clarity and not by way of limitation, and the procedures described are generally suitable for labeling any proteinaceous compound or substance, such as the reagent fetal restricted antigen herein.

Radiolabeled anti-(fetal restricted antigen) antibodies of this invention can be used for in vitro diagnostic tests. The specific activity of a tagged antibody depends upon the half-life, isotopic purity of the radioactive label and how the label is incorporated into the antigen or antibody. Table A lists several commonly used isotopes, their specific activities and half-lives. In immunoassay tests, the higher the specific activity, in general, the better the sensitivity.

TABLE A

| Isotope | Specific Activity of Pure Isotope (Curies/mole) | Half-Life |
|---|---|---|
| $^{14}C$ | $6.25 \times 10^1$ | 5720 years |
| $^{3}H$ | $2.91 \times 10^4$ | 12.5 years |
| $^{35}S$ | $1.50 \times 10^6$ | 87 days |
| $^{125}I$ | $2.18 \times 10^6$ | 60 days |
| $^{32}P$ | $3.16 \times 10^6$ | 14.3 days |
| $^{131}I$ | $1.62 \times 10^7$ | 8.1 days |

Procedures for labeling antibodies with radioactive isotopes listed in Table A are generally known in the art. Tritium labeling procedures are described in U.S. Pat. No. 4,302,438, for example. Iodinating, tritium labeling and ³⁵S labeling procedures especially adapted for antibodies are described by Goding, MONOCLONAL ANTIBODIES: PRINCIPLES AND PRACTICE. New York: Academic Press (1983) 124–126, and the references cited therein. Other procedures for iodinating antibodies are described by Hunter and Greenwood, *Nature.* 144:945 (1962) and David et al, *Biochem.* 13:1014–1021 (1974) and in U.S. Pat. Nos. 3,867,517 and 4,376,110. Examples of suitable systems, coupling procedures and substrate reactions therewith are disclosed in U.S. Pat. Nos. RE-31,006, 3,654,090, 4,214,048, 4,289,747, 4,302,438, 4,312,943, 4,376,110 and the references cited therein, for example. Examples of other suitable systems are described by Pesce et al, *Clin.Chem.* 20:353–359 (1974) and Wisdom, G., *Clin.-Chem.* 22:1243 (1976).

A list of suitable enzyme classes which can be used for labeling and specific examples for each class follow:

TABLE B

| Class | Enzyme Example |
|---|---|
| Hydrolases Carbohydrases | Amylases |
| Nucleases | Polynucleotidase |
| Amidases | Arginase |
| Purine deaminases | Adenase |
| Peptidases | Aminopolypeptidase |
| Proteinases | Pepsin |
| Esterases | Lipases |
| Iron Enzymes | Catalase |
| Copper Enzymes | Tyrosinases |
| Enzymes containing Coenzymes | Alcohol dehydrogenase |
| Enzymes reducing cytochrome | Succinic dehydrogenase |
| Yellow enzymes | Diaphorase |
| Mutases | Glyoxalase |
| Demolases | Aldolase |
| Oxidases | Glucose oxidase |
| | Horseradish peroxidase |
| Other enzymes | β-galactosidase |
| | Phosphatases |
| | Phosphorylases |
| | Hexokinases |

A list of suitable enzymes are described in Hawk et al, PRACTICAL PHYSIOLOGICAL CHEMISTRY, New York: McGraw-Hill pp 306–397 (1954).

Fluorogenic and chromogenic enzymes (enzymes in the presence of which a selected substrate will produce a fluorescent or chromogenic product) are useful labeling moieties. Methods for selectively conjugating enzymes to antibodies without impairing the ability of the antibody to bind with antigen and for conjugating enzymes to proteinaceous reagents are well known in the art.

Suitable enzymes and procedures for coupling them to antibodies are described by I. Chibata in IMMOBILIZED ENZYMES. Halsted Press: New York (1978); A. Cuatrecasas, *J.Bio.Chem.* 245:3059 (1970); Wilson, M. et al, INTERNATIONAL CONFERENCE IN IMMUNOFLUORESCENCE AND RELATED STAINING TECHNIQUES. W. Knapp et al, editors. Amsterdam: Elsevier pp 215–244 (1978); Sullivan, M. et al, *Ann.Clin.Biochem.* 16:221–240 (1979); Nygren, H. et al, *Med.Biol.* 57:187–191 (1979); Gadkari, D. et al, *J.Virol.Meth.* 10:215–224 (1985); Tijssen, P. et al, *Anal.Biochem.* 136:451–457 (1984); Tsuruta, J. et al, *J.Histochem.Cytochem.* 33:767–777 (1985); Ishikawa, E., *J.Immunoassay.* 4:209–327 (1983); and in U.S. Pat. No. 4,190,496, for example, the entire contents of the above listed references being hereby incorporated by reference in their entireties.

The preferred enzymes and suitable substrates corresponding thereto include horseradish peroxidase for which suitable substrates are o-phenylenediamine, m-phenylenediamine, o-dianisidine, and 4-chloro-α-napthol. They also include β-galactosidase for which suitable substrates are 4-methylumbelliferyl-β-D-galactoside, p-nitrophenyl-β-D-galactose, p-nitrophenol, o-nitrophenyl-β-D-galactose, and o-nitrophenol, for example. They include alkaline phosphatase for which suitable substrates are p-nitrophenylphosphate, indoxyl phosphate, and 5-bromo-3-chloroindoxyl phosphate, for example.

Examples of suitable procedures for enzyme labeling the antibody include the use of carbodiimides, dialdehydes, and gluteraldehyde bifunctional coupling reagents. Linkage of enzymes through amine groups can be achieved by treating the proteins with thionyl chloride, N-hydroxysuccinimide or similar reagents in an anhydrous solvent such as dimethylformamide, dioxane, dimethylsulfoxide, tetrahydrofuran, or the like. Alternative coupling agents include carbodiimides such as 1-ethyl-3-(3-(N,N'-dimethylamino)propyl)-carbodiimide, 1-cyclohexyl-3-(2-morpholinoethyl) carbodiimide methyl-p-toluenesulfonate, succinimidyl 4-(N-maleimidoethyl)-cyclohexane-1-carboxylate, and succinimidyl 3-(2-pyridyldithio)-propionate, for example.

The carbohydrate moiety of an enzyme can also be oxidized to an aldehyde and reacted with lysyl amino groups of immunoglobulins to form a Schiffs base. Reduction with sodium borohydride effects a stable linkage of enzyme and antibody. Horseradish peroxidase with antibody can be efficiently linked to immunoglobulins by the method of Wilson et al, INTERNATIONAL CONFERENCE IN IMMUNOFLUORESCENCE AND RELATED STAINING TECHNIQUES. W. Knapp et al, editors. Amsterdam: Elsevier pp 215–244 (1978).

Fluorophore and chromophore labeled antibodies can be prepared from standard fluorescent moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, *Science.* 162:526 (1968) and Brand, L. et al, *Ann.Rev.Biochem.* 41:843–868 (1972). The antibodies can be labeled with fluorescent chromophore groups by conventional procedures such as those disclosed in U.S. Pat. Nos. 3,940,475, 4,289,747 and 4,376,110, for example.

One group of fluorescers having a number of the desirable properties described above are the xanthene dyes, which include the fluoresceins derived from 3,6-dihydroxy-9-phenylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available.

Another group of fluorescent compounds are the naphthylamines, having an amino group in the alpha or beta position. Included among the naphthylamino compounds are 1-dimethylaminonaphthyl-5-sulfonate, 1-anilino-8-naphthalene sulfonate and 2-p-toluidinyl-6-naphthalene sulfonate. Other dyes include 3-phenyl-7-isocyanatocoumarin; acridines such as 9-isothiocyanatoacridine and acridine orange; N-[p-(2-benzoxazolyl)phenyl]maleimide; benzoxadiozoles such as 4-chloro-7-nitrobenzo-2-oxa-1,3-diazole and 7-(p-methoxybenzylamino)-4-nitrobenzo-2-oxa-1, 3-diazole; stilbenes such as 4-dimethylamino-4'-isothiocyanatostilbene and 4-dimethylamino-4'-maleimidostilbene; N,N'-dioctadecycloxacarboxyamine-p-toluenesulfonate; pyrenes such as 8-hydroxy-1,3,6-pyrenetrisulfonic acid, 1-pyrenebutyric acid, merocyanine 540, rose bengal, 2,4-diphenyl-3(2H)-furanone, o-phthaldehyde, as well as other readily available fluorescing molecules. These dyes either have active functionalities or such functionalities can be readily introduced.

For example, antibodies can be labeled with fluorochromes or chromophores by the procedures described by Goding (supra, pp 208-249). The concentration of fluorochrome is selected according to the table of Goding, MONOCLONAL ANTIBODIES: PRINCIPLES AND PRACTICE. New York: Academic Press (1983), p 229. For example, fluorescein isocyanate (1.0 mg/mL) or rhodamine isocyanate (10.0 mg/mL) in DMSO is prepared, and the desired volume (1-10% of total protein solution volume) is added to the protein solution dropwise, with stirring. The reaction proceeds for two hours, shielded from light. The product is purified by gel filtration on SEPHADEX G-25 gel in PBS containing 0.1% NaNO$_3$ to separate the unreacted or hydrolyzed fluorochrome. The absorbence of the conjugate is measured at 280 nm and at its peak in the visible region (495 nm for fluoresceinated antibody and 550 nm for rhodaminated antibody). The fluorochrome to protein ratio is calculated according to the procedure of Goding, MONOCLONAL ANTIBODIES: PRINCIPLES AND PRACTICE. New York: Academic Press (1983) pp 224-225. Conjugates are stored at 4° C. protected from light until use. If the antibody solution concentration is less than 1 mg/mL, BSA is added to the solution to a final concentration of 1 mg/mL.

The antibodies used in the methods of this invention can be covalently bonded to avidin or biotin in one embodiment of this invention. Suitable binding procedures involve cross-linking through a bifunctional cross-linking agent. Suitable bifunctional compounds are described by Peters, K. et al, *Ann.Rev.Biochim.* 46:523 (1977).

In other instances, the bonds can be formed directly between the reagents themselves. For example, antibody can be bound to biotin through functional groups on the respective materials. As a specific example, biotin can be treated with periodate and reacted with antibody to give a Schiff base formation without inhibiting the biotin to avidin binding or blocking immunological activity of the antibody. Avidin-conjugated and biotinylated reagents are available from Vector Laboratories, Burlingame, Calif.

Known techniques using bifunctional cross-linking agents include the following: (a) a one-step glutaraldehyde linkage, Avrameas, S., *Immunochem.* 6:43 (1969); (b) two-step glutaraldehyde linkage, Avrameas, S., *Immunochem.* 8:1175 (1971); and (c) dimaleimide linkage, Kato, K. et al, *Euro.J.Biochem.* 62:285 (1966).

Antibodies can be labeled with metallic radionuclides according the procedure of Hnatowich, D. et al, *J.Appl.Rad.* 35:554-557 (1984) and Buckley, R. et al, *Fed.Eur.-Biochem.Soc.* 166:202-204 (January, 1984). In this procedure the antibodies are conjugated with a chelating agent such as diethylenetriaminepentaacetic acid which is capable of forming a chelate with the metallic radionuclide. A suspension of 0.1 mg/mL of the bicyclic anhydride of DTPA (diethylenetriaminepentaacetic acid) is prepared in a dry solvent such as chloroform, ether or dry DMSO. An aliquot is removed to a clean, dry tube sufficient to provide a DTPA to immunoglobulin molar ratio of 1:1 and evaporated under nitrogen. A 10-20 μL (microliter) portion of the antibody solution used (10-20 mg/mL) in 0.05M bicarbonate buffer in saline, pH 7.0-7.5 is added to the dry DTPA, and the contents are agitated for 0.5-1.0 minute. The coupled protein preparation is diluted to 0.2 mL with the same buffer solution and purified on a 5 cm gel filtration column with SEPHADEX G-50 gel, using a saline eluant. The coupling efficiency is determined before purification by the addition of "chelation-grade" $^{111}$In in 0.5M acetate buffer solution, pH 6.0. Thin layer chromatography is used to separate the DTPA coupled antibody for calculation of the coupling efficiency. The DTPA-coupled antibodies can be stored at 4° C. until needed for binding with metallic radionuclides such as $^{111}$In+3, $^{212}$Bi+3 and $^{68}$Ga+3, for example.

One embodiment of the immunoassay methods of this invention uses an insoluble support such as a polystyrene plate to which anti-(fetal restricted antigen) antibody is adhered, either directly or through a goat anti-(mouse) antibody. It is contacted with a test sample diluted with an aqueous buffer solution such as phosphate buffer solution (PBS), pH 6 to 8 and preferably from 7.2 to 7.6 for a sufficient time to permit binding of fetal restricted antigen in the test sample with the anti-(fetal restricted antigen) antibody on the insoluble support, and then removing the sample from the support. The incubation time should be sufficient to permit substantial binding to occur, the time being temperature dependent. Suitable incubation times are from 30 to 240 minutes at temperatures within the range of from 16° to 40° C., the preferred contact time being at least 60 minutes at temperatures within the range of from 20° to 26° C.

The residual sample solution is then removed from the support by use of a rinse solution. Any conventional rinse solution can be used. A suitable rinse solution is described in U.S. Pat. No. 4,528,267. It is an aqueous phosphate buffer solution having a phosphate molarity of from 0.0001 to 0.05, a pH of from 6 to 8 and containing from 0.001 to 0.1 weight percent of nonionic surfactant. Suitable nonionic surfactants include polyoxyethylene ethers (BRIJ such as lauryl, cetyl, oleyl, stearyl, and tridecyl polyoxyethylene ethers); polyoxyethylene sorbitans (TWEEN such as polyoxyethylene sorbital monolaurate, monopalmitate, monostearate, monoleate, and trioleates); and other polyoxyethylene ethers (TRITON, for example). A preferred nonionic surfactant is octylphenoxypolyethoxy ethanol having 40 ethylene oxide units (TRITON X-405, Rohm and Hass Company).

The insoluble support is then contacted with a secondary antibody which will bind with the captured fetal restricted antigen on the insoluble support, i.e., a sandwiching antibody. The sandwiching antibody can be an anti-(fetal restricted antigen) antibody, or it can be an anti-(fetal restricted antigen class) antibody. The sandwiching antibody can be labeled or unlabeled. In the event that an unlabeled sandwiching antibody is used, an anti-(sandwiching antibody) tertiary antibody which binds with the sandwiching antibody and which bears a physically detectable label can be used in a conventional manner to determine the sandwiching antibody.

A variety of labels have been described above. For purposes of clarity and not by way of limitation, the subsequent steps of the process will be described for reagent antibodies which have been labeled with an enzyme, preferably a chromogenic or a fluorogenic enzyme. The term "chromogenic enzyme" is defined herein to refer to an enzyme which will produce a chromophore product with a suitable substrate. The term "fluorogenic enzyme" is defined herein to refer to an enzyme which will produce a fluorophore product with a suitable substrate.

The sandwiching antibody is applied to the insoluble support in an aqueous solution. The solution preferably contains suitable salts and buffers to preserve the reactants and facilitate the binding reaction. For example, the solution can contain bovine serum albumin (BSA), phosphate buffer solution (PBS), and a mild surfactant such as polyoxyethylene sorbitan ester employed in the above-described rinse solution. The incubation is continued for sufficient time to permit the sandwiching antibody to bind with exposed fetal restricted antigen epitopes, if any, adhering to the insoluble support. The preferred incubation times and temperatures are as set forth above for the binding of insolubilized reagent anti-(fetal restricted antigen) antibody with the test sample fetal restricted antigen.

The sandwiching antibody solution is then removed from the insoluble support, and the support is rinsed with a rinse solution such as is described above, to remove any residual, unbound material.

If the sandwiching antibody is unlabeled, an enzyme labeled anti-(sandwiching antibody) antibody or other binding agent which binds preferentially with the sandwiching antibody is applied to the insoluble support in an aqueous solution. The solution preferably contains suitable salts and buffers to preserve the reactants and facilitate the binding reaction. For example, the solution can contain bovine serum albumin (BSA), phosphate buffer solution (PBS), and a mild surfactant such as polyoxyethylene sorbitan ester employed in the above-described rinse solution. The incubation is continued for sufficient time to permit labeled anti-(fetal restricted antigen) antibody to bind with exposed fetal restricted antigen epitopes, if any, adhering to the insoluble support. The preferred incubation times and temperatures are as set forth above for the binding of insolubilized reagent anti-(fetal restricted antigen) antibody with the test sample fetal restricted antigen.

The labeled antibody solution is then removed from the insoluble support, and the support is rinsed with a rinse solution such as is described above, to remove any residual, unbound labeled material.

In a next step of the sandwich process of this invention, the insoluble support is contacted with an aqueous solution of a substrate which undergoes a reaction in the presence of the enzyme to release fluorescent or chromogen compound into the solution. Suitable substrates and the enzymes which they can be converted are described in U.S. Pat. Nos. 4,190,496 and 4,528,267, for example. The support is contacted with an aqueous solution of the substrate containing from $10^{-2}$ to $10^{-10}$ molar concentrations of the substrate. Substrate molar concentrations of from $10^{-4}$ to $10^{-5}$ are preferred. Preferred additional reagents and buffers in the substrate solution include 2-amino-2-methyl-1-propanol buffer, TRIS, and magnesium chloride, for example.

The substrate solution is incubated with the insoluble support for sufficient time for the reaction yielding the fluorophore or chromophore to occur. At temperatures of from 18° to 40° C., incubation times of from 5 to 240 minutes can be used. Preferably, the temperature is within the range of from 20° to 26° C., and the incubation time is from 30 to 120 minutes.

The fluorescent or chromophore level in the solution is then measured. The equipment and procedures for determining the level of fluorescence or chromophore level in the substrate solutions are those conventionally used in the art. The level of fluorescence or chromogen in solution is a function of the enzyme concentration on the insoluble support which is, in turn, a function of the amount of fetal restricted antigen in the test sample. The concentration of the fetal restricted antigen can be determined by comparing the fluorescence or chromophore level of the solution with respective fluorescence or chromophore levels obtained with control solutions containing known concentrations of fetal restricted antigen.

In an alternative embodiment of this invention, an insoluble support to which is adhered an antibody which captures a group of substances which include the fetal restricted antigen to be measured is contacted with a test sample diluted as described above. Residual sample solution is then removed from the support by use of a rinse solution, as described above. The insoluble support is then contacted with anti-(fetal restricted antigen) antibody which will bind preferentially with the captured fetal restricted antigen on the insoluble support. The anti-(fetal restricted antigen) antibody can be labeled or unlabeled. In the event that an unlabeled anti-(fetal restricted antigen) antibody is used, a tertiary antibody which binds with the sandwiching antibody and which bears a physically detectable label can be used in a conventional manner to determine the sandwiching antibody. The anti-(fetal restricted antigen) antibody is applied to the insoluble support in an aqueous solution, incubated, and rinsed to remove any residual, unbound material, as described above. If the anti-(fetal restricted antigen) antibody is unlabeled, an enzyme labeled anti-(sandwiching antibody) antibody or other binding agent which binds preferentially with the sandwiching antibody is applied to the insoluble support, incubated, excess antibody solution is removed from the insoluble support, and the support is rinsed, such as is described above, to remove any residual, unbound labeled material. The label is then determined by any means which is appropriate to the specific label used, and the amount of the analyte in the test sample is determined.

The binding of the anti-(fetal restricted antigen) antibody and the fetal restricted antigen in the test sample can also be determined by agglomeration of particles to which the anti-(fetal restricted antigen) antibody is adhered by fetal restricted antigen in the sample; precipitation of antibodies due to antibody-antigen reactions; or observations of physical or electrical changes which occur upon the antibody-antigen binding using semiconductor bridge probes, light disturbing patterns such as are described in U.S. Pat. No. 4,647,544, and the like.

In one embodiment of a membrane embodiment of the immunoassay methods of this invention, an insoluble support to which anti-(fibronectin) antibody is adhered is contacted with a test sample diluted with an aqueous buffer solution such as phosphate buffer solution (PBS), pH 6 to 8 and preferably from 7.2 to 7.6 for a sufficient time to permit binding of fetal restricted antigen in the test sample with the anti-(fetal restricted antigen) antibody on the insoluble support. The time required for binding is very small in a flow through system. Suitable incubation times can be one second up to 20 minutes at temperatures within the range of from 16° to 40° C., the preferred contact time being less than one minute and optimally from 10 seconds to 2 minutes.

The insoluble support is then contacted with an antibody which will bind with the captured fetal restricted antigen on the insoluble support, i.e., the sandwiching antibody. The sandwiching antibody can be labeled or unlabeled. In the event that an unlabeled sandwiching antibody is used, a tertiary antibody which binds with the sandwiching antibody and which bears a physically detectable label can be used in a conventional manner to determine the sandwiching antibody.

A variety of labels have been described above. For purposes of clarity and not by way of limitation, the subsequent steps of the process will be described for anti-(fetal restricted antigen) antibodies which have been labeled with an enzyme, preferably a fluorogenic or chromogenic enzyme.

The sandwiching antibody is applied to the insoluble support in an aqueous solution. The solution preferably contains suitable salts and buffers to preserve the reactants and facilitate the binding reaction. For example, the solution can contain bovine serum albumin (BSA), phosphate buffer solution (PBS), and a mild surfactant such as polyoxyethylene sorbitan ester employed in the above-described rinse solution. The incubation is continued for sufficient time to permit the sandwiching antibody to bind with exposed fetal restricted antigen epitopes, if any, adhering to the insoluble support. The preferred incubation times and temperatures are as set forth for the binding of insolubilized reagent anti-(fetal restricted antigen) antibody with the test sample fetal restricted antigen.

The sandwiching antibody solution optionally can be removed from the insoluble support, and the support is rinsed with a rinse solution such as described above, to remove any residual, unbound labeled material.

If the sandwiching antibody is unlabeled, an enzyme labeled anti-(sandwiching antibody) antibody or other binding agent which binds preferentially with the sandwiching antibody is applied to the insoluble support in an aqueous solution. The solution preferably contains suitable salts and buffers to preserve the reactants and facilitate the binding reaction. For example, the solution can contain bovine serum albumin (BSA), phosphate buffer solution (PBS), and a mild surfactant such as polyoxyethylene sorbitan ester employed in the above-described rinse solution. The incubation is continued for sufficient time to permit labeled anti-(sandwiching antibody) antibody to bind with exposed sandwiching antibody epitopes, if any, adhering to the insoluble support. The preferred incubation times and temperatures are as set forth above for the binding of insolubilized reagent anti-(fetal restricted antigen) antibody with the test sample fetal restricted antigen.

The labeled antibody solution is then removed from the insoluble support, and the support is rinsed with a rinse solution such as described above, to remove any residual, unbound labeled material.

In a next step of the sandwich process of this invention, the insoluble support is contacted with an aqueous solution of a substrate which undergoes a reaction in the presence of the enzyme to release fluorogen or chromogen compound into the solution. Suitable substrates and the enzymes which they can be converted are described in U.S. Pat. Nos. 4,190,496 and 4,528,267, for example. The support is contacted with an aqueous solution of the substrate containing from $10^{-2}$ to $10^{-10}$ molar concentrations of the substrate. Preferred additional reagents and buffers in the substrate solution include 2-amino-2-methyl-1-propanol buffer, TRIS, and magnesium chloride, for example.

The substrate solution is incubated with the insoluble support for sufficient time for the reaction yielding the fluorophore or chromophore to occur. At temperatures of from 18° to 40° C., incubation times of from 1 to 20 minutes can be used. Preferably, the temperature is within the range of from 20° to 26° C., and the incubation time is from 2 to 5 minutes. The fluorogen or chromogen level on the membrane can be measured using a reflectometer or densitometer.

Competition embodiments of this invention using labeled reagent fetal restricted antigen comprise contacting a mixture of the test sample and the labeled reagent fetal restricted antigen with an anti-(fetal restricted antigen) antibody adhered to an insoluble support, and determining the amount of label which either binds with the insoluble support or remains in the solution phase.

The competition embodiments of this invention using labeled anti-(fetal restricted antigen) antibodies can be of more than one form. One embodiment using anti-(fetal restricted antigen) antibody bound to the insoluble support comprises contacting a mixture of the test sample and labeled anti-(fetal restricted antigen) antibodies with an anti-(fetal restricted antigen) antibody adhered to an insoluble support, and determining the amount of label which either binds with the insoluble support or remains in the solution phase. Another embodiment using reagent fetal restricted antigen bound to the insoluble support comprises contacting a mixture of the test sample and labeled anti-(fetal restricted antigen) antibodies with a fetal restricted antigen adhered to an insoluble support, and determining the amount of label which either binds with the insoluble support or remains in the solution phase.

In each of these methods, the test sample is diluted with buffer solution, incubated and the label determined as described above with respect to the sandwich immunoassay embodiments. The concentration of the limiting reagent is selected to permit competitive binding between the reagents, with the amount of label remaining on the insoluble support or in the solution being a variable which is a function of the amount of the analyte in the test sample. These methods are generally well known and how to vary them to optimize a procedure are fully within the knowledge of a person skilled in the immunoassay art.

If fetal restricted antigen level determinations in the test sample are negative, the absence of normal uterine pregnancy is indicated. A determination of the presence of fetal restricted antigen in the test sample indicates pregnancy.

The kits of this invention generally comprise combinations of a support having reagents of this invention adhered thereto and a means for detecting nonrestricted pregnancy antigen in blood or urine. Sampling devices such as sampling swabs, and buffers for transport and storage can also be included. The individual parts of the kit may be packaged in any convenient form, such as vials, foil packages, or other containers. For example, insoluble support structures in a foil package can be combined with other reagents in vials or other packages. They can also be combined with other, optional reagents such as stop reagents in separate vials or other packages.

This invention is further illustrated by the following specific, but non-limiting examples. Temperatures are given in degrees Centigrade and percents as weight percents unless otherwise specified. Examples which are constructively reduced to practice herein are presented in the present tense, and examples representing laboratory experiments previously reduced to practice are presented in the past tense.

EXAMPLE 1

Polyclonal Antibodies

Fetal fibronectin is purified from amniotic fluid as described by Engvall and Ruoslahti, *Int.J.Cancer.* 20:1-5 (1977).

The anti-(fetal fibronectin) antibodies are elicited in rabbits using the immunization techniques and schedules described in the literature, e.g., Stollar, *Meth.Enzym.* 70:70 (1980), immunizing the rabbits with the fetal fibronectin antigen. The antiserum is screened in a solid phase assay similar to that used for monoclonal antibodies, e.g., as described by Lange et al, *Clin.Exp.Immunol.* 25:191 (1976) and Pisetsky et al, *J.Immun.Meth.* 41:187 (1981).

The IgG fraction of the antisera is purified further by affinity chromatography using CNBr-Sepharose 4B (Pharmacia Fine Chemicals) to which has been coupled fetal fibronectin. The method used for coupling is that recommended by the gel manufacturer, AFFINITY CHROMATOGRAPHY. Pharmacia Fine Chemicals, pp 15-18.

The column is equilibrated with from 2 to 3 volumes of buffer (0.01M PBS, pH 7.2), and the anti-(fetal fibronectin) antibody containing solution is then applied to the column. The absorbency of the eluate is monitored at 280 nm until protein no longer passes from the column. The column is then washed with 0.1M glycine buffer, pH 2.5, to desorb the immunoaffinity bound anti-(fetal fibronectin) antibody. Peak protein fractions are collected, pooled and dialyzed against 0.01M PBS, pH 7.2, for 24-36 hour at 4° C. with multiple buffer changes.

If a higher purity is desired, the affinity purified IgG can be passed through an adult plasma fibronectin bound affinity column by the procedure described above to remove any antibodies which would cross-react with adult plasma fibronectins.

EXAMPLE 2

Monoclonal Antibody

Using the purified fetal fibronectin obtained by the procedure of Example 1, mouse monoclonal antibodies to the fetal fibronectin are obtained using standard procedures of Galfre and Milstein, *Meth.Enzym.* 73:1 (1981) and Matsuura and Hakomori, *Proc.Natl.Acad.Sci.USA.* 82:6517-6521 (1985), using fetal fibronectin as the antigen for immunizing the mice. The monoclonal antibodies are screened using a modification of the techniques described in the literature, e.g., Lange et al, Clin.Exp-.Immunol. 25:191 (1976) and Pisetsky et al, *J.Immun.Meth.* 41:187 (1981).

Mouse monoclonal antibody is purified from ascites fluid or from hybridoma culture supernatants using Protein-A coupled Sepharose-4B (Pharmacia Fine Chemicals) according to the procedure of Tijsson, PRACTICE AND THEORY OF ENZYME IMMU-NOASSAYS. Elsevier Science Publishers, pp 105-107 (1985).

EXAMPLE 3

Polyclonal Antibody Coated Microtiter Plate

Rabbit anti-(fetal fibronectin) prepared and further purified to remove adult fibronectin cross-reactivity as described in Example 1 is diluted to 10 $\mu$g/mL in 0.05M carbonate buffer, pH 9.6. 100 $\mu$L is dispersed into each well of an IMMULON II microtiter plate (Dynatech). The plate is covered and incubated 4 hr at room temperature or 4° C. overnight. The plate is washed 4 times with Wash Buffer (0.02M Tris HCl, 0.015M NaCl, 0.05% TWEEN-20), filling and emptying the wells completely with each use. The plate is then blocked by dispersing into each well 200 $\mu$L of a Blocking Solution (0.01M PBS, 1% BSA, 0.02% $NaN_3$, pH 7.4) and incubating for 1 hour at room temperature. The wells are then washed 4 times with Wash Buffer, as described above. The plate is now ready for immunoassay of test samples.

EXAMPLE 4

Monoclonal Antibody Coated Microtiter Plate

Goat F(ab')$_2$ anti-(mouse IgG) antibody (Tago) is diluted to 10 $\mu$g/mL in 0.05M carbonate buffer, pH 9.6. 100 $\mu$L is dispersed into each well of an IMMULON II microtiter plate (Dynatech). The plate is covered and incubated 4 hour at room temperature or 4° C. overnight. The plate is washed 4 times with Wash Buffer as described in Example 3. The plate is then blocked by dispensing into each well the Blocking Solution as described in Example 3. Mouse monoclonal anti-(fetal fibronectin) ascites prepared as in Example 2 is diluted 1/5000 with 0.01M PBS-1% BSA, pH 7.4. 100 $\mu$L of the solution is dispensed into each well of the blocked microtiter plate. The wells are incubated, covered, for 2 hour at room temperature or overnight at 4° C. The plate is then washed 4 times with Wash Buffer as described above, and is then ready for immunoassay of test samples.

EXAMPLE 5

Enzyme Labeled Antibody

Anti-(fetal restricted antigen) antibody prepared in accordance with the procedures of Example 1 or Example 2 is conjugated with alkaline phosphatase following the one-step glutaraldehyde procedure of Avrameas, Immunochem. 6:43 (1969).

EXAMPLE 6

Pregnancy Test

A sample is removed from the vaginal cavity in the vicinity of the cervical canal or cervical os, and assayed to determine the presence of a fetal restricted antigen. The presence of such fetal restricted antigen in the sample indicates that the patient is pregnant.

Positive and negative controls are included in the test. The positive control is amniotic fluid of known fetal fibronectin concentration, appropriately diluted to fall within the assay range (20 ng/mL to 5 $\mu$g/mL for a monoclonal based assay). The negative control is sample diluent. The Assay Standard is amniotic fluid of known fibronectin concentration, serially diluted in sample diluent to provide a standard curve, ranging from 20 ng to 5 μg/mL.

The sample diluent is the solution described in U.S. patent application Ser. No. 244,969, filed Sep. 15, 1988, the entire contents of which are hereby incorporated by reference. It protects fibronectin-containing test samples from proteolytic degradation during transit and storage. The solution consists of 0.05M Tris-HCl, pH 7.4; 0.15M NaCl; 0.02% NaN$_3$; 1% BSA; 500 Kallikrein Units/mL of aprotinin; 1 mM phenylmethylsulfonyl fluoride (PMSF) and 5 mM EDTA.

Swab samples are collected from the vicinity of the cervical os and are immersed in 0.75 mL of sample diluent in a collection vial. The swabs are removed from the solution for the assay, and the solution is centrifuged at 13,000 rpm for 5 minutes to remove particulates. The supernatant contains any fetal fibronectin which was in the swab.

A microtiter plate prepared as in Example 3 or 4 is used for the assay. 100 μL of each standard, sample, positive and negative control are placed in separate wells and incubated 2 hours at room temperature. The plate is washed 4 times with Wash Buffer as described in Examples 3 and 4. 100 μL of alkaline phosphatase-conjugated goat anti-(human fibronectin) prepared as in Example 5 is diluted 1/1000 in Conjugate Buffer (0.02M Tris-HCl, pH 8; 0.3M NaCl; 0.05% TWEEN 20; 5% BSA; 0.02% NaN$_3$). 100 μL is dispensed into each well and incubated for 2 hour at room temperature. The plate is washed 4 times as previously described. 4 mg/mL of p-nitrophenylphosphate (PNPP) is used as the substrate. This is diluted in 0.18M 2-amino-2-methyl-1-propanol (AMP) buffer, pH 9.5 with 0.12 mM MgCl$_2$. 100 μL is dispensed into each well of the microtiter plate. After 5 minutes incubation at room temperature, the reaction rate in milli-OD/min is read at 405 nm on a V-MAX ™ kinetic microtiter plate reader (Molecular Devices).

A standard curve is constructed by correlating increasing reaction rate with increasing fibronectin concentration in the standards. Unknowns are calculated directly from the curve or by using a pre-set computer program such as is available from Molecular Devices.

Samples obtained before week 20 of pregnancy which demonstrate significant fetal fibronectin in the test sample indicate normal uterine pregnancy. Samples in which significant amounts of fetal fibronectin are absent indicate that normal uterine pregnancy is not present.

We claim:

1. A method for determining normal intrauterine pregnancy during the first 20 weeks of pregnancy comprising
   a) obtaining a test sample from the vaginal cavity; and
   b) determining the presence of fetal fibronectin in the sample, the presence of fetal fibronectin indicating the presence of intrauterine pregnancy.
2. The method of claim 1 wherein the sample is obtained from the vicinity of the cervical canal.
3. The method of claim 1 wherein the sample is obtained from the vicinity of the cervical os.
4. The method of claim 1 comprising the steps of
   a) contacting the sample with an anti-(fetal fibronectin) antibody for a time sufficient to permit antigen-antibody binding to occur; and
   b) determining the presence of said binding.
5. The method of claim 4 comprising the steps of
   a) contacting the sample with an insoluble support to which anti-(fetal fibronectin) antibody is adhered for a time sufficient to permit antigen-antibody binding to occur, and removing the sample from the support;
   b) contacting the insoluble support with an anti-fibronectin antibody for a time sufficient to permit antigen-antibody binding to occur, and removing unbound anti-fibronectin antibody from the support; and
   c) determining the presence of anti-fibronectin antibody on the insoluble support.
6. The method of claim 5 wherein the anti-fibronectin antibody has a physically detectable label.
7. The method of claim 5 wherein the presence of anti-fibronectin antibody is determined by
   a) contacting the insoluble support with a labeled antibody which binds preferentially with the anti-fibronectin antibody and removing unbound labeled antibody from the support; and
   determining the presence of the label on the insoluble support.
8. The method of claim 1 comprising the steps of
   a) contacting the sample with an insoluble support to which anti-fibronectin antibody is adhered for a time sufficient to permit antigen-antibody binding to occur, and removing the sample from the support;
   b) contacting the insoluble support with an anti-(fetal fibronectin) antibody for a time sufficient to permit antigen-antibody binding to occur, and removing unbound anti-(fetal fibronectin) antibody from the support; and
   c) determining the presence of anti-(fetal fibronectin) antibody on the insoluble support.
9. The method of claim 8 wherein the anti-(fetal fibronectin) antibody has a physically detectable label.
10. The method of claim 8 wherein the presence of anti-(fetal fibronectin) antibody is determined by
    a) contacting the insoluble support with a labeled antibody which binds preferentially with the anti-(fetal fibronectin) antibody, and removing unbound labeled antibody from the support; and
    determining the presence of the label on the insoluble support.

* * * * *

UNITED STATES PATENT AND TRADEMARK OFFICE
CERTIFICATE OF CORRECTION

PATENT NO. : 5,185,270
DATED : February 9, 1993
INVENTOR(S) : Senyei, et al.

It is certified that error appears in the above-identified patent and that said Letters Patent is hereby corrected as shown below:

▶ Column 3, line 34:   delete "$\epsilon_1$" and insert -- $\beta_1$ --.

▶ Column 6, line 33:   after "1988," insert -- now U.S. Patent No. 5,096,830 issued on March 17, 1992 --.

▶ Column 21, line 4:   after "1988," insert -- now U.S. Patent No. 5,096,830 issued on March 17, 1992 --.

Signed and Sealed this

Twenty-fifth Day of January, 1994

*Attest:*

BRUCE LEHMAN

*Attesting Officer*   Commissioner of Patents and Trademarks